(12) United States Patent
Lord et al.

(10) Patent No.: US 8,808,243 B2
(45) Date of Patent: Aug. 19, 2014

(54) IMPLANTABLE INFUSION DEVICE WITH MULTIPLE CONTROLLABLE FLUID OUTLETS

(75) Inventors: Peter C. Lord, Valencia, CA (US);
Stephen D. Das, Santa Clarita, CA (US);
Scott R. Gibson, Granada Hills, CA (US)

(73) Assignee: Medallion Therapeutics, Inc., Valencia, CA (US)

( * ) Notice: Subject to any disclaimer, the term of this patent is extended or adjusted under 35 U.S.C. 154(b) by 0 days.

(21) Appl. No.: 13/182,412

(22) Filed: Jul. 13, 2011

(65) Prior Publication Data

US 2011/0270233 A1    Nov. 3, 2011

Related U.S. Application Data

(63) Continuation of application No. 11/420,641, filed on May 26, 2006, now Pat. No. 8,002,747.

(60) Provisional application No. 60/685,126, filed on May 26, 2005.

(51) Int. Cl.
*A61M 37/00*    (2006.01)
*A61M 5/142*    (2006.01)
*A61M 5/168*    (2006.01)

(52) U.S. Cl.
CPC ....... *A61M 5/14276* (2013.01); *A61M 5/16827* (2013.01)
USPC ........................................ 604/131; 604/891.1

(58) Field of Classification Search
USPC ................ 604/131–133, 890.1, 891.1, 891.2, 604/65–67
See application file for complete search history.

(56) References Cited

U.S. PATENT DOCUMENTS

| | | | |
|---|---|---|---|
| 3,126,031 A | 3/1964 | Hayner | |
| 4,003,379 A | 1/1977 | Ellinwood | |
| 4,072,146 A | 2/1978 | Howes | |
| 4,193,397 A | 3/1980 | Tucker et al. | |
| 4,373,527 A | 2/1983 | Fischell et al. | |
| 4,443,218 A | 4/1984 | DeCant et al. | |
| 4,449,983 A | 5/1984 | Cortese et al. | |
| 4,588,394 A | 5/1986 | Schulte et al. | |
| 4,634,427 A | 1/1987 | Hannula et al. | |
| 4,718,893 A * | 1/1988 | Dorman et al. ................. | 604/67 |
| 4,871,351 A | 10/1989 | Feingold | |
| 4,894,057 A | 1/1990 | Howes et al. | |
| 5,207,642 A | 5/1993 | Orkin et al. | |
| 5,240,713 A | 8/1993 | Ayer | |
| 5,607,393 A | 3/1997 | Ensminger et al. | |
| 5,718,678 A | 2/1998 | Fleming et al. | |
| 6,436,091 B1 | 8/2002 | Harper | |
| 6,471,688 B1 | 10/2002 | Harper | |

(Continued)

FOREIGN PATENT DOCUMENTS

| | | |
|---|---|---|
| EP | 1520595 A1 | 4/2005 |
| WO | WO 02/072178 A1 | 9/2002 |
| WO | WO 2005/002642 A2 | 1/2005 |
| WO | WO 2005/007223 A2 | 1/2005 |

*Primary Examiner* — Kevin C Sirmons
*Assistant Examiner* — Phillip Gray
(74) *Attorney, Agent, or Firm* — Henricks, Slavin & Holmes LLP

(57) ABSTRACT

An implantable infusion system includes at least two controllable fluid transfer devices that may be used to transfer different fluid flows to the same or different body sites.

23 Claims, 5 Drawing Sheets

(56) References Cited

U.S. PATENT DOCUMENTS

| | | |
|---|---|---|
| 6,520,936 B1 | 2/2003 | Mann |
| 6,554,822 B1 | 4/2003 | Holschneider et al. |
| 6,652,510 B2 | 11/2003 | Lord et al. |
| 6,902,544 B2 | 6/2005 | Ludin et al. |
| 7,083,593 B2 | 8/2006 | Stultz |
| 7,131,967 B2 | 11/2006 | Gray et al. |
| 8,002,747 B2 | 8/2011 | Lord et al. |
| 2001/0020471 A1 | 9/2001 | Kitten |
| 2002/0156462 A1 | 10/2002 | Stultz |
| 2002/0188327 A1 | 12/2002 | Struble |
| 2004/0143242 A1* | 7/2004 | Ludin et al. ............. 604/891.1 |
| 2005/0113745 A1 | 5/2005 | Stultz |
| 2006/0271021 A1* | 11/2006 | Steinbach ............. 604/891.1 |

* cited by examiner

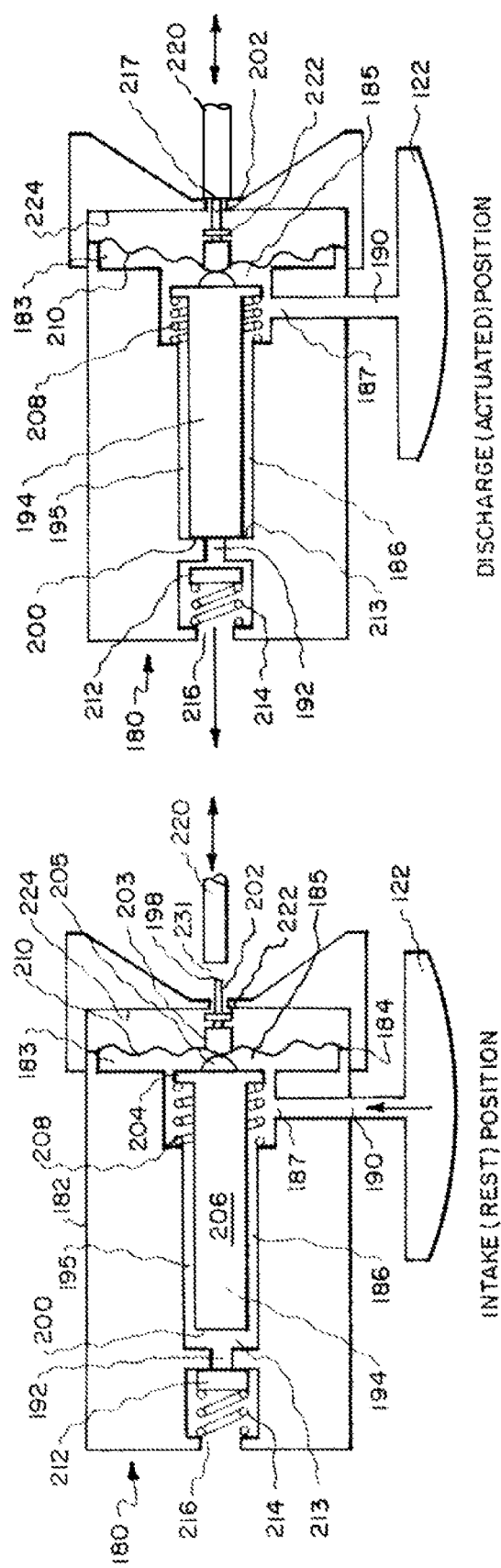

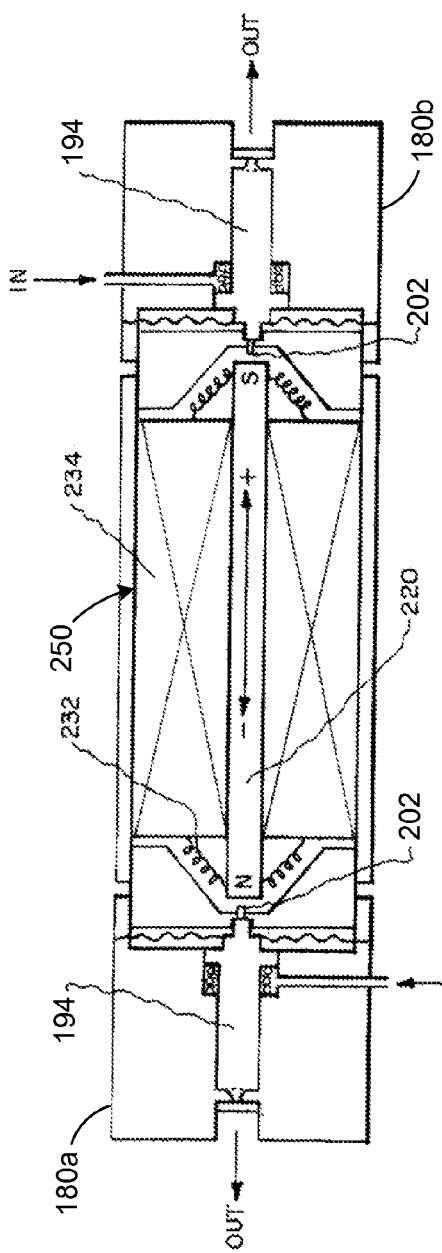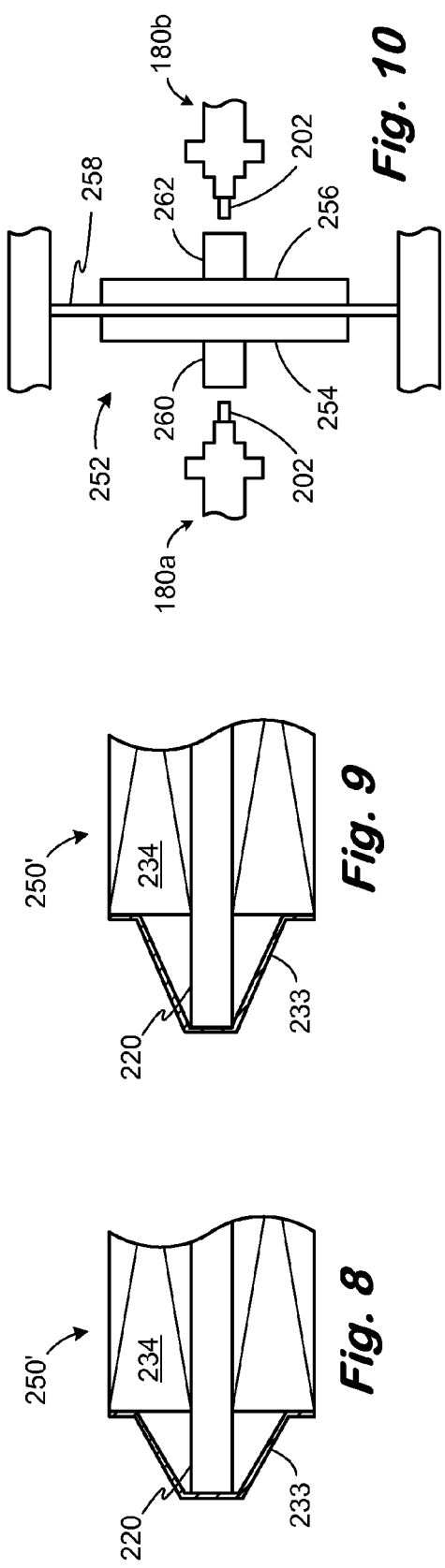

US 8,808,243 B2

IMPLANTABLE INFUSION DEVICE WITH MULTIPLE CONTROLLABLE FLUID OUTLETS

CROSS-REFERENCE TO RELATED APPLICATIONS

This application is a continuation of U.S. application Ser. No. 11/420,641, now U.S. Pat. No. 8,002,747. filed May 26, 2006, which claims the benefit of and priority to previously filed U.S. Provisional Patent Application Ser. No. 60/685,126, filed May 26, 2005, which is entitled "Implantable Infusion Device With Multiple Controllable Outlets," both of which are incorporated herein by reference in their entirety.

FIELD OF THE INVENTIONS

The present inventions relate generally to implantable infusion devices.

BACKGROUND OF THE INVENTIONS

Implantable infusion devices typically include a housing containing a medication reservoir which can be filled transcutaneously by a hypodermic needle penetrating a fill port septum. The medication reservoir is generally coupled via an internal flow path to a device outlet port for delivering medication through a catheter to a patient body site. Typical infusion devices also include a controller and a fluid transfer mechanism, such as a pump or a valve, for moving the medication from the reservoir through the internal flow path to the device's outlet port. The use of such implantable infusion devices has been well established in pain management, and therapies such as diabetes control, where a single medication is delivered to a single body site.

In other therapies, it is desirable to deliver the same medication to two different body sites, such as cisplatinum to the ovaries for ovarian cancer, either at the same rate or at different rates. In yet other therapies, there is a need to deliver two or more distinct medications to different body sites or to the same site independently. For example, with some pain management protocols, it is desirable to deliver morphine and clonidine to a patient's intrathecal site. In certain cancer therapies, it may be desirable to deliver multiple medications to multiple sites. As a further example, in diabetes therapy, insulin and glucogon may be administered sequentially to lower or to raise blood sugar respectively.

SUMMARY OF THE INVENTIONS

An implantable infusion device in accordance with one of the present inventions includes a medication reservoir and at least two controllable fluid transfer devices for respectively transferring first and second fluid flows to the same or different body sites. Each fluid transfer device, such as a pump mechanism or a valve mechanism, includes an inlet that may be coupled to a reservoir and an outlet that may be coupled to a catheter for delivering a measured flow to a body site. Such an infusion device may be used to, for example, deliver a single medication under different protocols to a single body site, deliver a single medication to multiple body sites, deliver multiple medications to multiple body sites, deliver multiple medications to a single body site, simultaneously deliver multiple medications at different rates, and/or deliver one medication at a constant rate and another medication at a variable rate.

An implantable infusion device in accordance with one of the present inventions includes a medication reservoir with two or more compartments. Adjacent compartments, which may be used to store different fluids for delivery to the same or different body sites, are separated by a pressure transmissive partition so that they experience the same pressure. There are a variety of advantages to such a device. For example, the use of a common reservoir with two or more compartments saves space. Insuring that the reservoirs remain at equal pressures obviates safety concerns that can be associated with variations in pressure from one compartment to the other. The use of a pressure transmissive partition also simplifies the overall design of the infusion device because. More specifically, by maintaining one of compartments at the desired pressure, the infusion device will actually maintain all of the compartments at the desired pressure.

An implantable infusion device in accordance with one of the present inventions includes multiple fluid transfer devices that are actuated by a common actuator. Such a device is particularly advantageous because it greatly reduces the amount of space within the device that must be dedicated to the actuation of the fluid transfer devices.

BRIEF DESCRIPTION OF THE DRAWINGS

FIG. 5 is a schematic diagram of a pump head in accordance one embodiment of a present invention in a fluid intake position.

FIG. 6 is a schematic diagram of a pump head in accordance one embodiment of a present invention in a discharge position.

FIG. 7 is a schematic diagram of a pair of fluid transfer devices with a common actuator in accordance one embodiment of a present invention.

FIG. 8 is a schematic diagram of a portion of a common actuator in accordance one embodiment of a present invention.

FIG. 9 is a schematic diagram of a portion of the common actuator illustrated in FIG. 8 in an actuation mode.

FIG. 10 is a schematic side view of a portion of an infusion device in accordance with one embodiment of a present invention.

DETAILED DESCRIPTION

Figure 1:
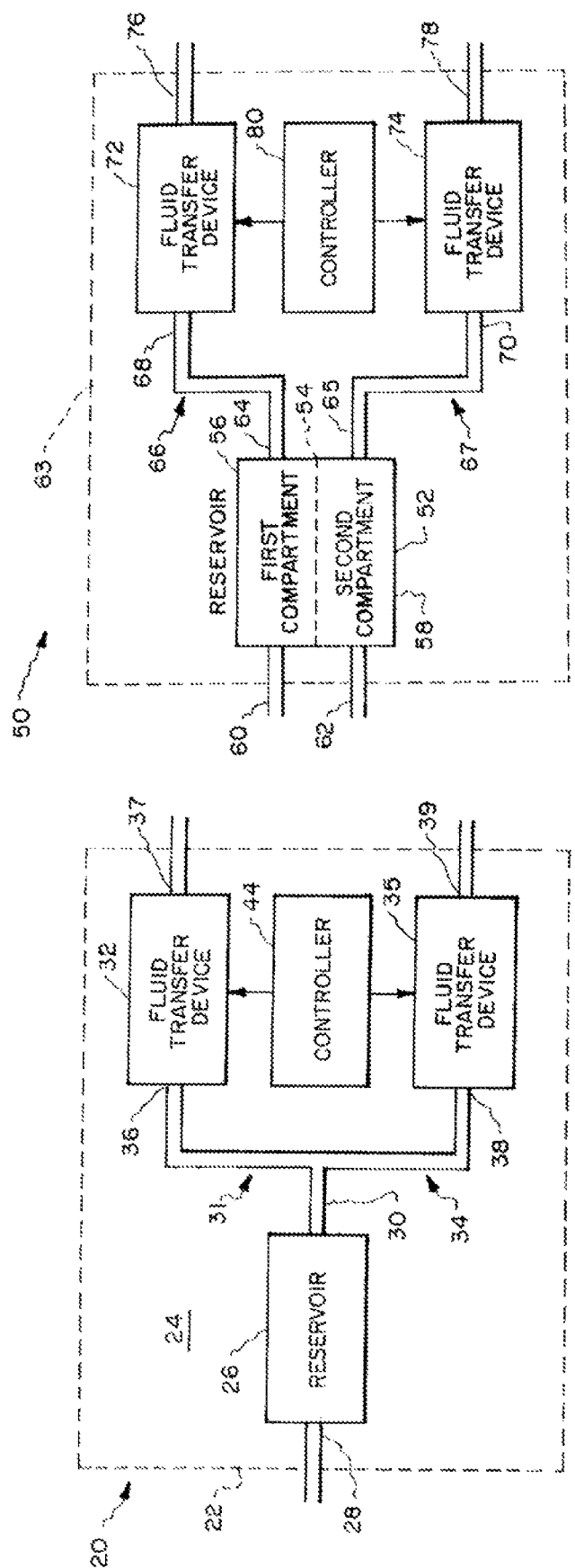
FIG. 1A is a block diagram of an implantable infusion device in accordance with one embodiment of a present invention.
FIG. 1B is a block diagram of an implantable infusion device in accordance with one embodiment of a present invention.

As illustrated for example in FIG. 1A, an implantable infusion device 20 in accordance with one embodiment of a present invention includes an outer shell 22 enveloping an interior volume 24. A fluid reservoir 26, which is defined within the internal volume 24, has a fill port 28 opening through the outer shell 22. Fluid medication is supplied through the fill port 28 (e.g., via a hypodermic needle) to the reservoir 26 for storage. The fluid reservoir 26 in the illustrated embodiment supplies two separate fluid transfer devices. More specifically, the fluid reservoir 26 includes a discharge port 30 that is coupled to a first fluid transfer path 31 including a first fluid transfer device 32. The discharge port 30 is also coupled to a second fluid transfer path 34 including a second fluid transfer device 35. The first fluid transfer device 32 defines an inlet 36 and an outlet 37. Similarly, the second fluid transfer device 35 defines an inlet 38 and an outlet 39. The outlets 37 and 39 open through the outer shell 22 and are adapted to communicate with respective catheters for delivering medication from the reservoir 26 to the same or different body sites.

The exemplary fluid transfer devices 32 and 35 are controllable devices, such as selectively actuatable pumps and/or valve mechanisms, which can be independently operated by a common controller 44, such as a microprocessor, in accordance with different stored medication profiles, or protocols, that are accessible by the common controller. Each such profile can, for example, define delivery start times, delivery durations, delivery rates and other parameters. Thus, the independent operation of two or more fluid transfer devices allows the implantable infusion device 20 (as well as those discussed below) to, for example, deliver a single medication under different protocols to a single body site, deliver a single medication to multiple body sites, deliver multiple medications to multiple body sites, deliver multiple medications to a single body site, simultaneously deliver multiple medications at different rates, and/or deliver one medication at a constant rate and another medication at a variable rate, typically in accordance with a stored profile. The fluid transfer paths 31 and 34 can additionally include various functional components, such as a pressure regulator and/or sensor, to promote patient safety and device efficacy, as is discussed in detail below in the context of the embodiment illustrated in FIG. 2.

As illustrated for example in FIG. 1B, an implantable infusion device 50 in accordance with one embodiment of a present invention includes a reservoir 52 having an interior partition 54 forming first and second compartments 56 and 58 which can store different first and second medications. Compartments 56 and 58 include respective fill ports 60 and 62 which open through the device shell 63, and through which medications can be supplied to fill the compartments. The compartments 56 and 58 are also respectively provided with discharge ports 64 and 65, which are coupled to respective fluid transfer paths 66 and 67. The fluid transfer paths 66 and 67 include the inlets 68 and 70 of fluid transfer devices 72 and 74. The fluid transfer devices 72 and 74 also include outlets 76 and 78 that are adapted to communicate through the device shell 63 with respective catheters for delivering the first and second medications to the same or different body sites. As is discussed below with reference to FIG. 2, the fluid transfer paths 66 and 67 may also include various functional components that promote patient safety and device efficacy. The fluid transfer devices 72 and 74 are controlled by a controller 80 to produce independent medication flows from outlets 76 and 78, where each such flow conforms to a stored delivery profile accessed by the controller.

One example of a suitable fluid transfer device is a pump mechanism with a fluid chamber and a pump element mounted for movement between an intake position for drawing fluid from the reservoir into the fluid chamber, and a discharge position for discharging fluid from the chamber to an outlet. The pump element can, for example, comprise a piston mounted for movement by a controlled actuator.

Examples of piston-based pumps are discussed below. It should be noted, however, that piston-based pumps in accordance with the present inventions are not limited to such examples, and that embodiments of the inventions may include pumps that are not piston-based.

Figure 2:
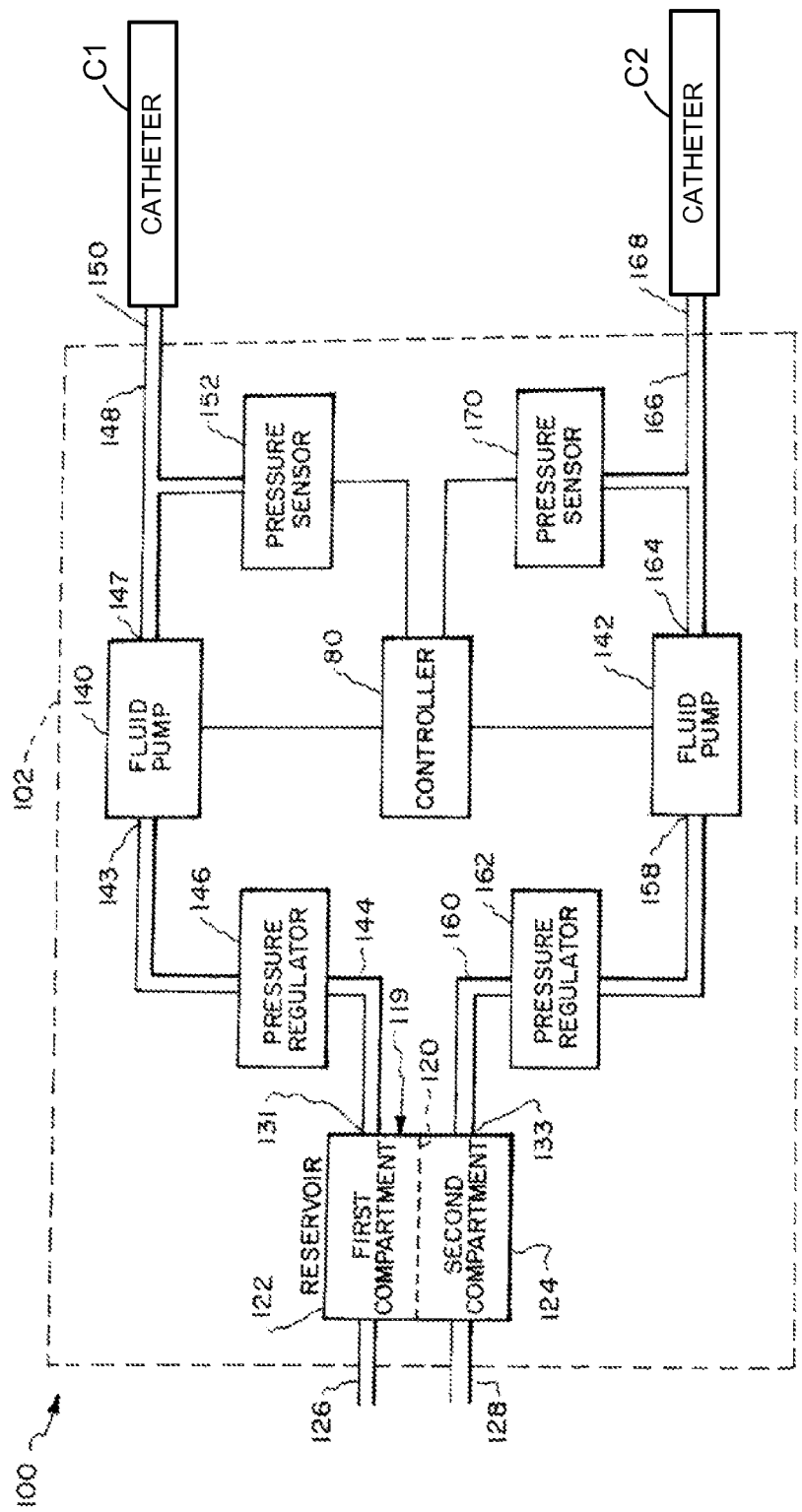
FIG. 2 is a block diagram of an implantable infusion device in accordance with one embodiment of a present invention.

Turning to FIG. 2, an implantable infusion device 100 in accordance with one embodiment of a present invention includes a reservoir 119 having an interior partition 120 forming first and second compartments 122 and 124 which can store different first and second medications. Compartments 122 and 124 include respective fill ports 126 and 128, which open through the device shell 102 and through which medications can be supplied to fill the compartments. The compartments 122 and 124 are also respectively provided with discharge ports 131 and 133, which are coupled to respective fluid transfer paths 144 and 160. The fluid transfer paths 144 and 160 include the inlets 143 and 158 of fluid pumps 140 and 142. The fluid pumps 140 and 142 also include outlets 147 and 164 that are adapted to communicate through the device shell 102 with respective catheters C1 and C2 for delivering the first and second medications to the same or different body sites. The exemplary fluid transfer paths 144 and 160 also include respective pressure regulators 146 and 162 which prevent overpressurization in the reservoir from impacting the pumps or downstream fluid flow. Respective pressure sensors 152 and 170 are also provided for monitoring pressure to, for example, detect catheter blockages or leaks. The fluid pumps 140 and 142 are controlled by a controller 80 to produce independent medication flows from outlets 150 and 168 via fluid passageways 148 and 166, where each such flow conforms to a stored delivery profile accessed by the controller.

Figure 4A:
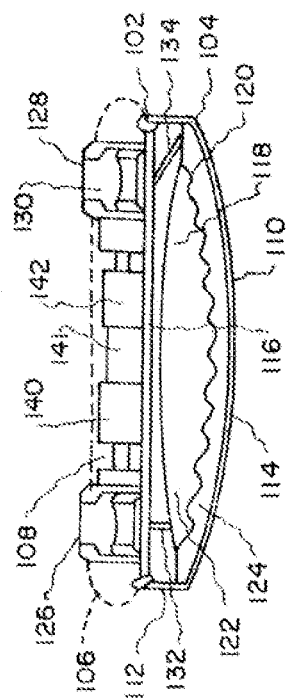
FIG. 4A is a schematic sectional view taken substantially along plane 4A-4A in FIG. 3.
Figure 3:
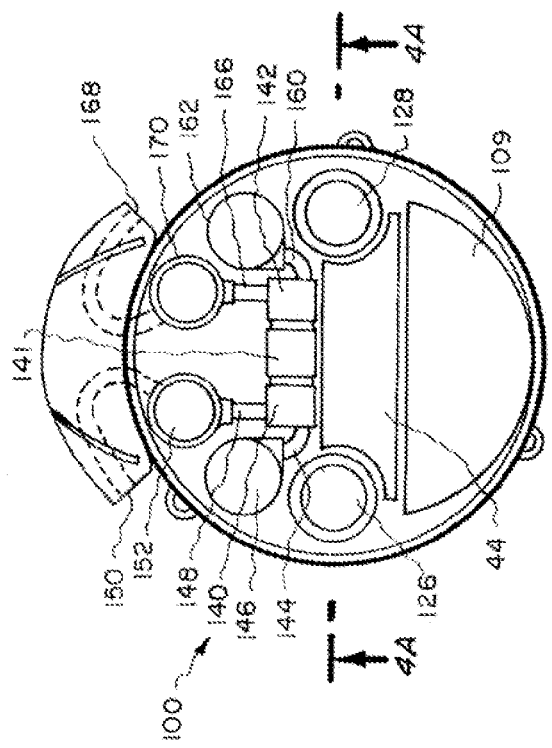
FIG. 3 is a schematic plan view of an implantable infusion device in accordance with one embodiment of a present invention.

FIGS. 3 and 4A schematically depict a structural configuration of an exemplary implantable infusion device 100, shown in block diagram form in FIG. 2, that can produce first and second independently controllable medication outflows. The device 100 includes a housing or shell 102 with a cup shaped lower member 104 and a detachable cup shaped upper, or cover, member 106. The housing upper member 106 is shown with a dashed line in FIG. 4A and is omitted from FIG. 3 for the sake of clarity. The housing lower and upper members 104 and 106 are configured to mate with one another to enclose a volume 108 for accommodating the components depicted in FIG. 2 together with a battery 109 or other suitable power source. The exemplary housing 102, which is sized for implantation into a human body, will typically be about 1 to 3 inches long and about 1 to 3 inches wide (or 1 to 3 inches in diameter) and less than about 1.5 inches thick.

The lower housing member 104 in the exemplary implantable infusion device 100 includes an outer wall 110 with a stiff axially extending ring portion 112 and a cross wall portion 114 extending laterally across the bottom edge of the ring portion. The top edge of the ring portion 112 supports, and is closed by, a mounting board 116, e.g., a circuit board. Thus the housing member 104 defines a closed sealed volume 118 between the lower surface of mounting board 116 and the interior surface of the lower housing cross wall portion 114.

The sealed volume 118 contains an interior partition 120 between a first reservoir compartment 122 and a second reservoir compartment 124. These compartments are intended to be suitably sealed so that they can respectively accommodate and isolate different first and second medications and/or different concentrations of the same medication, as discussed in greater detail below.

In the exemplary embodiment illustrated in FIGS. 3 and 4A, first and second fill ports 126 and 128 are supported on the mounting board 116. Each fill port includes a self healing septum 130 which is accessible through cover portion 106 for piercing by a hypodermic needle. The first fill port 126 communicates via passageway 132 with the first reservoir compartment 122. Similarly, the second fill port 128 communicates via passageway 134 with the second reservoir compartment 124.

As illustrated for example in FIG. 3, first and second fluid transfer devices, such as pump heads 140 and 142 with an electromagnetic actuator 141 mounted on the board 116 between the pump heads, may be provided. In the illustrated embodiment, the fluid inlet 143 (FIG. 2) of pump head 140 is coupled via a fluid passageway 144, which may include a pressure regulator 146, to the interior of the first compartment 122. The fluid outlet 147 (FIG. 2) of pump head 140 is coupled via a fluid passageway 148 to a first device outlet port 150 adapted for coupling to a first catheter. The fluid passageway 148 may include a pressure sensor 152. In operation, actuation of the pump head 140 transfers fluid from reservoir compartment 122 past pressure regulator 146 and pressure sensor 152 to device outlet port 150. Port 150 is preferably configured for coupling to catheter C1 for delivery to an internal body site.

Similarly, the fluid inlet 158 (see FIG. 2) of pump head 142 is coupled via a fluid passageway 160, which may include a pressure regulator 162, to the interior of the second reservoir compartment 124. The fluid outlet 164 (see FIG. 2) of pump head 142 is coupled via a fluid passageway 166 to a second device outlet port 168 adapted for coupling to a second catheter. The fluid passageway 166 may include a pressure sensor 170. Actuation of the pump head 142 acts to transfer fluid from reservoir compartment 124 to device outlet port 168, through catheter C2, and to a body site.

Although the embodiment illustrated in FIGS. 3 and 4A includes pump heads 140 and 142, which enable fluid to be transferred from a reservoir compartment held at ambient or negative pressure, other types of fluid transfer devices may be employed. For example, if the reservoir compartments are held at a positive pressure, then the fluid transfer devices could comprise controlled valves. The prior art shows various types of infusion devices using positive pressure and negative pressure reservoirs for medication delivery. The positive and negative pressures are typically produced by suitable propellants, such as biphasic propellants.

In one exemplary embodiment, a negatively biased ambient pressure reservoir of the type generally described in International Application WO 2005/002642, published 13 Jan. 2005, may be employed. The '642 application describes an infusion device in which a medication reservoir has a movable wall which is exposed to ambient pressure. The reservoir is configured with a bias device, such as a spring, for exerting a force to produce a resultant interior pressure which is always negative with respect to the ambient pressure.

Such a negatively biased ambient pressure is achieved in the embodiment illustrated in FIGS. 3 and 4A by forming the lower housing cross wall portion 114 of a flexible spring material biased to bow outwardly. The outer surface of cross portion 114 is exposed to a positive ambient pressure $F_A$ which acts in a direction tending to collapse the cross portion 114. The inherent spring bias force $F_B$ of the cross portion 114 acts in a direction opposite to the ambient force $F_A$ to produce an interior pressure in compartment 124 equal to:

$$P_C = (F_A - F_B)/\text{Area}$$

The exemplary partition 120 illustrated in FIGS. 3 and 4A is formed of a pressure transmissive material and, accordingly, is a pressure transmissive partition. As a consequence, the interior pressure in compartment 122 will equal the interior pressure in compartment 124, which will be negative with respect to ambient pressure acting against the exterior surface of cross portion 114. In other words, the partition 120 performs the function of equalizing the pressure within the compartments 122 and 124. The exemplary partition 120 has a wavy bellows-like shape, or some other non-linear shape, that allows the partition to adjust in size in response to volumetric changes within the compartments 122 and 124 in such a manner that the pressure transmissive material is not itself substantially stretched.

With respect to materials, examples of suitable pressure transmissive materials include flexible impermeable polymeric films, i.e. flexible films that do not diffuse solutes or liquids. Specific examples include polyvinylidene film, polyvinylidene fluoride (PVDF) film, polyvinylidene chloride (PVDC) film, polytetrafluoroethylene film such as Teflon® film, high density polyethylene film, and fluoropolymer film such as Halar® film. The films will typically be about 0.002 inch thick, but the actual thickness will depend on the material employed and the intended application.

Figure 4B:
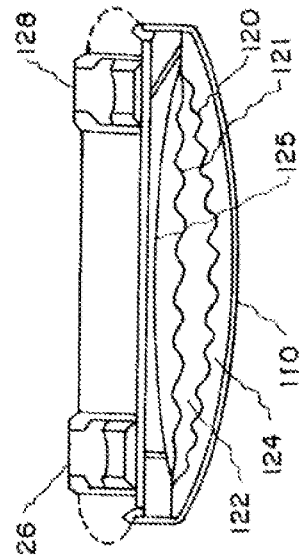
FIG. 4B is a schematic sectional view similar to FIG. 4A with an alternate reservoir configuration.

An alternative reservoir configuration is illustrated in FIG. 4B. Here, the reservoir includes three compartments. A first reservoir compartment 122 is separated from a second reservoir compartment 124 by a first pressure transmissive partition 120, and a third reservoir compartment 125 is separated from the second reservoir compartment 124 by a second pressure transmissive partition 121. It should be appreciated that the reservoir can be configured with still additional compartments to suit the intended application. Moreover, it should be understood that since the multiple compartments are exposed to the same pressure, the pressure source, e.g., propellant or ambient pressure, can be associated with any one of the compartments.

Figure 4C:
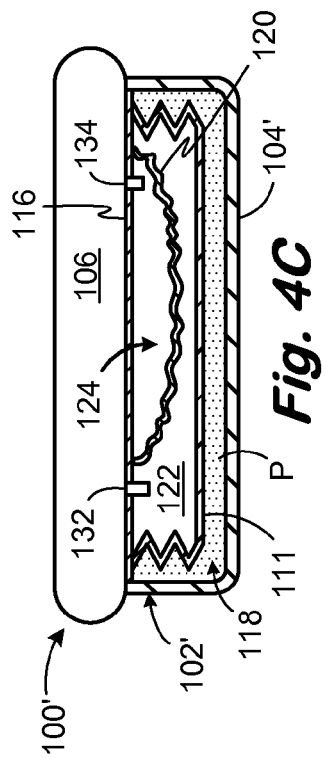
FIG. 4C is a schematic partial sectional view similar to FIG. 4A with an another alternate reservoir configuration.

As noted above, positive and negative reservoir pressures may be produced by a suitable propellant. One example of an implantable infusion device with a propellant based pressurization arrangement is generally represented by reference numeral 100' in FIG. 4C. The implantable infusion device 100' is substantially identical to the implantable infusion device 100 illustrated in FIGS. 3 and 4A and similar elements are represented by similar reference numerals. Here, however, the lower member 104' of the shell 102' does not include the aforementioned flexible cross-wall portion. Instead, an reservoir enclosure 111 with titanium bellows is positioned within the sealed volume 118, and a pressure transmissive partition 120 is positioned within the reservoir enclosure. The pressure transmissive partition 120 divides the reservoir within the reservoir enclosure 111 into a first reservoir compartment 122 and a second compartment 124. The remainder of the sealed volume 118 is occupied by propellant P, which may be used to exert positive or negative pressure on the reservoir enclosure 111. Here too, the pressure within the first and second compartments 122 and 124 will be equalized by the pressure transmissive partition 120.

Turning to FIGS. 5 and 6, an exemplary pump head 180 has a fluid intake (rest) position and a fluid discharge (actuated) position. The pump head 180 may, for example, be used as the pump head 140 and/or the pump head 142 described above with reference to FIGS. 3 and 4. The pump head 180 may be actuated by a variety of different actuators. One such actuator is the common actuator 250, which is discussed in detail below with reference to FIG. 7 and includes the hammer 220 illustrated in FIGS. 5 and 6. Alternatively, in those instances where two or more pump heads are employed, each pump head may be paired with its own individual actuator, if desired.

The exemplary pump head 180 includes a block 182 defining a bore 183 extending inwardly from block end face 184. The bore 183 includes an inlet chamber 185 leading into a piston channel 186. A fluid intake port 187 opens into piston channel 186 from a passageway 190 coupled to a fluid source, e.g., reservoir compartment 122. Channel 186 is configured to open into a reduced channel outlet port 192. A piston 194 is mounted in channel 186 for reciprocal linear movement, i.e. from the quiescent intake (rest) position illustrated in FIG. 5 to the actuated discharge position illustrated in FIG. 6, and back to the intake (rest) position. The clearance space 195 between the piston 194 and the piston channel 186 should be minimized to insure efficient and consistent fluid volume discharge per stroke. The piston 194 has a strike end 198 (at the right as viewed in FIG. 5) and a pressure end or face 200 (at the left). The strike end 198 in the illustrated embodiment includes a reduced diameter strike pin portion 202 extending from a greater diameter energy transfer portion 203. The portions 202 and 203 are retained by a spring diaphragm 210 which seals the bore 183. The piston 194 has a flange 204 carrying a ball portion 205 aligned with energy transfer portion 203. A return spring 208 bears against the left face of flange 204 urging it to the right to engage portions 203 and 205. The spring diaphragm 210 assists in centering the piston body 206 in channel 186 and establishing the quiescent intake (rest) position of the piston 194.

A pump chamber 213 is defined between the piston pressure face 200 and the channel outlet port 192. An elastomeric check valve element 212, normally urged closed by spring 214, is mounted between channel outlet port 192 and the pump head outlet 216.

In one exemplary implementation of the pump head 180, the pump chamber volume is approximately 0.25 microliters. When actuated by the hammer 220 axially striking the free end 217 of the strike pin portion 202, piston pressure face 200 moves approximately 0.20 millimeters within approximately 2 milliseconds or less to force a fluid volume (stroke volume) of approximately 0.25 microliters out through port 192 to the pump head outlet 216. To optimize the transfer of energy from hammer 220 to pin portion 202, it is preferable to provide a small gap 231 between the hammer 220 and the strike pin portion 202 to build up kinetic energy. The gap 231 can be adjusted by including a stroke adjustment shim 222 which can be variably positioned along the portion 202 for engaging stop surface 224.

More particularly, assume that the pump head 180 is initially in the quiescent intake (rest) position depicted in FIG. 5. In this position, fluid from the reservoir compartment 122 fills passageway 190 and, via port 187, the bore 183 including inlet chamber 185, the clearance space 195 surrounding piston 194, and the pump chamber 213. When the pump head 180 is actuated such that hammer 220 drives piston 194 from the position illustrated in FIG. 5 to the position illustrated in FIG. 6, the pressure face 200 forces pump chamber fluid through channel outlet port 192 and past valve element 212 to pump head outlet 216. The clearance space 195 is minimized (e.g., approximately 5.0 microns or less) so that most of the fluid in the pump chamber 213 is forced out through outlet port 192 with only a small portion moving back though the clearance space 195 to passageway 190 and the reservoir compartment 122.

As should be appreciated, the axial hammer force required to actuate the pump head, i.e. to move the piston 194 from the position illustrated in FIG. 5 to the position illustrated in FIG. 6, must transfer sufficient energy to:
1) Deflect diaphragm 210,
2) Compress return spring 208,
3) Compress valve spring 214, and
4) Overcome head pressure at the pump head outlet 216 which can, for example, include some degree of occlusion in a downstream catheter.

Also, the return spring 208 and diaphragm 210 must provide a sufficient axial restoration force to return the piston 194 from the discharge (actuated) position illustrated in FIG. 6 to the intake (rest) position illustrated in FIG. 5 once the hammer force has terminated.

The axial force applied to strike pin 202 to actuate the pump head 180 can be produced by various mechanisms. One example of a such a mechanism is a common actuator 250 illustrated in FIG. 7. The common actuator 250, which includes the aforementioned hammer 220, may be used to actuate a pair of pump heads 180.

As used herein, a "common actuator" is a single device that can be associated with a plurality of pump heads or other fluid transfer devices and actuated in more than one actuation mode to independently drive (or not drive) each of the fluid transfer devices. More specifically, a common actuator that is used in combination with a first and second fluid transfer devices may have a first actuation mode that actuates the first fluid transfer device to discharge fluid while the second fluid transfer device remains unactuated, a second actuation mode that causes the second fluid transfer device to discharge fluid while the first fluid transfer device remains unactuated, and a neutral mode. The term "neutral mode" describes a state where common actuator (or a portion of the common actuator) is in a position or condition that results in both fluid transfer devices remaining unactuated. In the exemplary context of the pump heads, a common actuator that is used in combination with first and second pump heads may have a first actuation mode that drives the first pump head to discharge fluid while the second pump head remains in the intake position, a second actuation mode that drives the second pump head to discharge fluid while the first pump head remains in the intake position, and a neutral mode that allows both pump heads to remain in their respective intake positions. An actuation cycle occurs when the common actuator transitions from the neutral mode to the first (or second) actuation mode and back to the neutral mode. Depending on the desired actuation rate, the common actuator may remain in the neutral mode at the end of the actuation cycle for a predetermined period before beginning the next actuation cycle. Alternatively, at the end of an action cycle, the common actuator will immediately begin the next actuation cycle.

A common actuator may be used to drive different pump heads (or other fluid transfer devices) at the same rate or at different rates. With respect to driving the pump heads at the same rate, this may be accomplished by simply alternating between the first and second modes, with or without pauses in the neutral mode between each actuation cycle or between some combination of actuation cycles. Different pump head driving rates may be accomplished by actuating one pump head more frequently than the other. For example, the common actuator could be operated such that the first actuation mode occurs twice for each occurrence of the second actuation mode. Another exemplary actuation regimen is useful in those instances where one medication is dispensed at a regular interval (or constant rate) and another medication is dispensed at a variable rate, e.g. in response to a predetermined bodily condition or patient request. Here, the common actuator could be actuated in the first actuation mode at the regular interval and only actuated in the second actuation mode in response to the predetermined bodily condition or patient request.

Referring again to FIG. 7, and although common actuators are not so limited, one example of a common actuator that may be used to actuate first and second pump heads 180a and 180b, which are identical to pump head 180 and shown here in simplified form, is the common actuator 250. In the first actuation mode, the hammer 220 is linearly driven in a first direction to actuate the first pump head 180a and, in the second actuation mode, the hammer is linearly driven in a second direction to actuate the second pump head 180b. The second pump head 180b will remain in the intake position during the first actuation mode, while the first pump head 180b will remain in the intake position during the second actuation mode. The common actuator 250 also has a neutral mode, where neither of the pump heads 180a and 180b are actuated. The common actuator 250 is shown in the neutral mode in FIG. 7.

The hammer 220 in the illustrated embodiment is a rod of magnetic material (i.e. an armature) that is suspended by spring mounts 232. The hammer 220 also extends axially through a fixedly positioned coil winding 234. In the first actuation mode, current is driven through the coil winding 234 in one direction and the resulting electromagnetic force propels the hammer 220 in the first direction against the strike pin 202 of pump head 180a. The spring mounts 232 will return the hammer 220 to the neutral position when current flow ends (e.g. about 20-100 milliseconds after it begins in some embodiments), thereby completing the actuation cycle. Current is driven through the coil winding 234 in the opposite direction in the second actuation mode. The resulting electromagnetic force propels the hammer 220 in the second direction against the strike pin 202 of pump head 180b. Here too, the spring mounts 232 will return the hammer 220 to the neutral position when current flow ends. The current driven through the coil winding 234 may be controlled by a suitable controller such as, for example, the controller 44 (FIG. 1) or the controller 80 (FIG. 2).

The common actuator illustrated in FIG. 7 is merely one example of a common actuator that may be used to selectively drive two or more fluid transfer devices. With respect to those which employ electromagnetic force to selectively drive a hammer, one alternative is a moving coil actuator. Here, a magnet is held in a fixed position and a coil moves relative thereto. A hammer is carried by the coil, or individual hammers may be carried at opposite ends of the coil, for movement with the coil. Another alternative is illustrated in FIGS. 8 and 9. Here, instead of the aforementioned spring mounts 232, the common actuator 250' (which is otherwise identical to actuator 250), includes resilient membranes 233 (only one shown in FIGS. 8 and 9) or other resilient devices that are positioned over the longitudinal ends of the hammer 220. The resilient membranes 233 perform the same functions as the spring mounts 232. More specifically, when the current induced electromagnetic force that drives the hammer 220 from the position illustrated in FIG. 8 to the strike position illustrated in FIG. 9, and stretches the membrane 233 is removed, the membrane will drive the hammer back to the position illustrated in FIG. 8.

Another exemplary common actuator that may be used to selectively actuate first and second fluid transfer devices is generally represented by reference numeral 252 in FIG. 10. Although the common actuator 252 may be used in combination with a variety of fluid transfer devices, pump heads 180a and 180b are shown for purposes of illustration. The actuator 252, which is in its neutral mode orientation in FIG. 10, includes first and second piezoceramic disks 254 and 256 that are carried by a flexible diaphragm 258. The piezoceramic disks 254 and 256 carry hammers 260 and 262. In the first actuation mode, a voltage is applied across the piezoceramic disk 254, thereby causing the disk to bend in the first direction (i.e. to the left in FIG. 10). The hammer 260 will, in turn, strike the strike pin 202 of the pump head 180a and drive the associated piston to the discharge position. The piezoceramic disk 254, as well the remainder of the common actuator 252, will return to the neutral mode illustrated in FIG. 10 when the voltage is removed. Similarly, in the second actuation mode, a voltage is applied across the piezoceramic disk 256, thereby causing the a disk to bend in the second direction (i.e. to the right in FIG. 10). The hammer 262 will, in turn, strike the strike pin 202 of the pump head 180b and drive the associated piston to the discharge position.

Other piezo-type common actuators may also be employed. By way of example, a single piezoceramic disk that bends in opposite directions based on the polarity of the applied voltage, and has unbent neutral state, may be carried on the flexible diaphragm 258 in place of the disks illustrated in FIG. 10. Cantilevered piezo elements, which are another alternative, eliminate the need for the flexible diaphragm. Additionally, in any piezo-type common actuator, the hammer(s) may be eliminated so that a piezoceramic element strikes the strike pin 202 or the corresponding portion of some other fluid transfer device. Piezo-type common actuators may also be employed in those instances where the fluid transfer devices are microelectromechanical system (MEMS) based pumps or valves.

Common actuators that may be used to selectively actuate a plurality of fluid transfer devices are not limited to those which move linearly back and forth. For example, rotary cam actuators that have, for example, left, right and neutral positions may be employed. An actuator that relies on the heat triggered expansion of a gas, such as air, may also be used as common actuator for selectively actuating two or more fluid transfer devices.

Although the inventions disclosed herein have been described in terms of the preferred embodiments above, numerous modifications and/or additions to the above-described preferred embodiments would be readily apparent to one skilled in the art. By way of example, but not limitation, in some applications it may be desirable to utilize a single pump mechanism and an appropriate valve arrangement to produce controlled fluid flows from multiple reservoir compartments. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. An infusion device configured for implantation in a patient's body, the infusion device comprising:
   a housing;
   a pressure source associated with the housing;
   a reservoir in the housing including at least first and second reservoir compartments, the first and second reservoir compartments being positioned relative to one another and relative to the pressure source such that the pressure source acts directly on the first reservoir and the first reservoir separates the pressure source from the second reservoir;
   a pressure transmissive interior partition between the first and second reservoir compartments configured to equalize pressure within the first and second reservoir compartments;

a first fluid transfer device operably connected to the first reservoir compartment and to a first fluid outlet;

a second fluid transfer device operably connected to the second reservoir compartment and to a second fluid outlet; and a controller that controls at least one of the first and second fluid transfer devices.

2. The device of claim 1 wherein the pressure source comprises a propellant that produces a consistent positive pressure.

3. The device of claim 1 wherein the pressure source comprises a propellant that produces a consistent negative pressure.

4. The device of claim 1 wherein the pressure source comprises a pressure transmissive outer wall configured to negatively bias the pressure in the compartments relative to the ambient pressure.

5. The device of claim 1 further comprising
a third reservoir compartment; and
a pressure transmissive interior partition between the second and third reservoir compartments configured to equalize pressure within the second and third reservoir compartments.

6. The device of claim 1, wherein the pressure transmissive interior partition comprises a flexible polymeric membrane.

7. The device of claim 1, wherein the pressure transmissive interior partition has a wavy shape.

8. The device of claim 1, wherein
the first fluid transfer device comprises a pump.

9. The device of claim 1, wherein
the first fluid transfer device comprises a first pump; and
the second fluid transfer device comprises a second pump.

10. The device of claim 1, wherein
the first fluid transfer device comprises a valve.

11. The device of claim 1, wherein
the first fluid transfer device comprises a first valve; and
the second fluid transfer device comprises a second valve.

12. The device of claim 1, wherein
the first fluid outlet comprises a first catheter port; and
the second fluid outlet comprises a second catheter port.

13. The device of claim 12, wherein
the first and second catheter ports are located in spaced relation to one another.

14. The device of claim 1 further comprising:
a first drug in the first reservoir compartment; and
a second drug in the second reservoir compartment.

15. The device of claim 1 wherein
the pressure source comprises a resilient member having an exterior surface that is exposed to ambient pressure and an interior surface;
the resilient member interior surface and the pressure transmissive interior partition define the first reservoir compartment;
the resilient member is self-biased away from the first reservoir compartment with enough force to create a pressure within the first reservoir compartment that is negative with respect to the ambient pressure; and
the second reservoir compartment is completely separated from the resilient member by the pressure transmissive interior partition.

16. The device of claim wherein
the second reservoir compartment is located within the first reservoir compartment.

17. The device of claim 1 further comprising
a first fluid passageway that connects the first reservoir compartment to the first fluid transfer device; and
a second fluid passageway that connects the second reservoir compartment to the second fluid transfer device.

18. The device of claim 1 wherein
wherein the pressure source is the only non-pump pressure source associated with the first and second reservoir compartments.

19. An infusion device configured for implantation in a patient's body, the infusion device comprising:
a housing;
a reservoir in the housing including at least first and second reservoir compartments;
a first pump connected to the first drug reservoir compartment by a first passageway and connected to a first catheter port;
a second pump connected to the second drug reservoir compartment by a second passageway and connected to a second catheter port;
means, located between the first and second drug reservoir compartments, for equalizing pressure within the first and second drug reservoir compartments; and
a controller that controls at least one of the first and second pumps.

20. The device of claim 19, wherein
the first and second catheter ports are located in spaced relation to one another.

21. The device of claim 19 further comprising:
a first drug in the first drug reservoir compartment; and
a second drug in the drug second reservoir compartment.

22. The device of claim 19 wherein
the housing includes a resilient member having an exterior surface that is exposed to ambient pressure and an interior surface;
the resilient member interior surface and the means for equalizing pressure define the first drug reservoir compartment;
the resilient member is self-biased away from the first drug reservoir compartment with enough force to create a pressure within the first drug reservoir compartment that is negative with respect to the ambient pressure; and
the second drug reservoir compartment is completely separated from the resilient member by the means for equalizing pressure.

23. The device of claim 19 wherein
the first drug reservoir compartment is directly exposed to a non-pump source of negative pressure; and
the second drug reservoir compartment is not directly exposed to a non-pump source of negative pressure.

* * * * *